United States Patent
Reaungamornrat et al.

(10) Patent No.: US 11,854,158 B2
(45) Date of Patent: Dec. 26, 2023

(54) MEDICAL IMAGE ENHANCEMENT

(71) Applicant: Siemens Healthcare GmbH, Erlangen (DE)

(72) Inventors: Sureerat Reaungamornrat, Plainsboro, NJ (US); Andrei Puiu, Brasov (RO); Lucian Mihai Itu, Brasov (RO); Tommaso Mansi, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 329 days.

(21) Appl. No.: 16/773,213

(22) Filed: Jan. 27, 2020

(65) Prior Publication Data
US 2020/0311869 A1 Oct. 1, 2020

(30) Foreign Application Priority Data
Mar. 25, 2019 (EP) .................... 19464005

(51) Int. Cl.
| | | |
|---|---|---|
| *G06T 3/40* | (2006.01) | |
| *G16H 30/40* | (2018.01) | |
| *G06N 20/20* | (2019.01) | |
| *G06N 3/08* | (2023.01) | |
| *G06N 3/045* | (2023.01) | |

(52) U.S. Cl.
CPC ........... *G06T 3/4046* (2013.01); *G06N 3/045* (2023.01); *G06N 3/08* (2013.01); *G06N 20/20* (2019.01); *G16H 30/40* (2018.01)

(58) Field of Classification Search
CPC . G06T 2207/20081; G06T 2207/20084; G06T 11/001; G06T 2207/10024; G06T 2207/10016; G06T 7/246; G06T 7/254; G06T 7/194; G06T 7/248; G06T 2207/10101; G06T 7/0012; G06T 2207/20221
USPC ....................................................... 382/254
See application file for complete search history.

(56) References Cited

U.S. PATENT DOCUMENTS

| | | | |
|---|---|---|---|
| 2011/0058719 A1* | 3/2011 | Trzasko | G06T 11/006 382/128 |
| 2016/0210749 A1 | 7/2016 | Nguyen et al. | |
| 2017/0337682 A1 | 11/2017 | Liao et al. | |
| 2018/0158209 A1 | 6/2018 | Fine et al. | |
| 2018/0218502 A1 | 8/2018 | Golden et al. | |
| 2018/0225822 A1 | 8/2018 | Zhou et al. | |
| 2019/0057521 A1 | 2/2019 | Teixeira et al. | |
| 2019/0238648 A1* | 8/2019 | Goel | F16K 17/06 |
| 2019/0365498 A1* | 12/2019 | Gibby | A61B 90/90 |

(Continued)

OTHER PUBLICATIONS

Izuka et al., "Globally and Locally Consistent Image Completion", http://hi.cs.waseda.ac.jp/~iizuka/projects/completion/data/completion_sig2017.pdf, ACM Transactions on Graphics, vol. 36, No. 4, Article 107; Jul. 2017, 14 pgs.

(Continued)

*Primary Examiner* — Ajibola A Akinyemi

(57) ABSTRACT

Systems and methods are provided for enhancing a medical image. An initial medical image having an initial field of view is received. An augmented medical image having an expanded field of view is generated using a trained machine learning model. The expanded field of view comprises the initial field of view and an augmentation region. The augmented medical image is output.

18 Claims, 10 Drawing Sheets

(56) References Cited

U.S. PATENT DOCUMENTS

2019/0378276 A1* 12/2019 Flossmann ............... G06T 7/33
2021/0224997 A1* 7/2021 Kushida ................. G06T 5/001

OTHER PUBLICATIONS

Isola et al., "Image-to-Image Translation with Conditional Adversarial Networks", Computer Vision Foundation, 2017, https://arxiv.org/pdf/1611.07004.pdf, Nov. 26, 2018 pp. 1125-1134.
Yang et al., "High-Resolution Image Inpainting Using Multi-Scale Neural Patch Synthesis", Computer Vision Foundation, https://arxiv.org/pdf/1611.09969, Apr. 13, 2017, pp. 6721-679.
Wang et al., "Discriminitive Region Proposal Adversarial Networks for High-Quality Image-to-Image Translation", https://arxiv.org/pdf/1711.09554.pdf, Aug. 6, 2018, 16 pgs.
Pathak et al., "Context Encoders: Feature Learning by Inpainting", Nov. 21, 2016, https://arxiv.org/pdf/1604.07379.pdf, 12 pgs.
Xie et al., "Image Denoising and Inpainting with Deep Neural Networks", China, https://papers.nips.cc/paper/4686-image-denoising-and-inpainting-with-deep-neural-networks.pdf, 9 pgs.
Yeh et al., "Semantic Image Inpainting with Deep Generative Models", Jul. 13, 2017, https://arxiv.org/pdf/1607.07539.pdf, 19 pgs.
Sogancioglu et al., "Chest X-ray Inpainting with Deep Generative Models", https://openreview.net/pdf?id=HJzbN-2oz, 1st Conference on Medical Imaging with Deep Learning (MIDL 2018), Amsterdam.
Unberath et al., "Deep Learning-based Inpainting for Virtual DSA", IEEE Nuclear Science Symposium and Medical Imaging Conference, 3 pgs.
Goodfellow et al., "Generative Adversarial Nets", 2014, 9 pgs.
Salimans et al., "Improved Techniques for Training GANs", Jun. 10, 2016, https://arxiv.org/pdf/1606.03498.pdf, 10 pgs.
Radford et al., "Unsupervised Representation Learning with Deep Convolutional Generative Adversarial Networks", Jan. 7, 2016, https://arxiv.org/pdf/1511.06434.pdf, 16 pgs.
Li et al., "Precomputed Real-Time Texture Synthesis with Markovian Generative Adversarial Networks", Apr. 15, 2016, https://arxiv.org/pdf/1604.04382.pdf, 17 pgs.
Soltanayev et al., "Training Deep Learning Based Denoisers without Ground Truth Data", May 23, 2018, https://arxiv.org/pdf/1803.01314.pdf, 10 pgs.
Gondara, Lovedeep, "Medical Image Denoising Using Convolutional Denoising Autoencoders", https://arxiv.org/pdf/1608.04667 pdf, Sep. 18, 2016, 6 pgs.
Nasrollahi et al., "Deep Learning based Super-Resolution for Improved Action Recognition", Computer Vision Center, Spain, 2015, 6 pgs.
Ronneberger et al., "U-Net: Convolutional Networks for Biomedical Image Segmentation", May 18, 2015, https://arxiv.org/pdf/1505.04597.pdf, 8 pgs.
Chollet, Francois, "Deep Learning with Python", Manning Shelter Island, 2018, pp. 1-15, 297-302.
European Search Report dated Oct. 15, 2019 in corresponding European Patent Application No. 19464005.8.
Johannes Kopf et al: "Quality prediction for image completion". ACM Transactions on Graphics, vol. 31. No. 6, Nov. 1, 2012 (Nov. 1, 2012). pp. 1-8.
Krishna Paudel: Stitching of X-ray Thesis Uppsala Universitet, Nov. 1, 2012 (Nov. 1, 2012). pp. 1-78.
Ge Yunhao et al: "Unpaired whole-body MR to CT synthesis with correlation coefficient constrained adversarial earning". Progress in Biomedical Optics and Imaging, SPIE—International Society for Optical Engineering, Bellingham, WA, US, vol. 10949, Mar. 15, 2019; pp. 1094905-1094905.
Van Den Oord, et al.; "Pixel Recurrent Neural Networks", Aug. 19, 2016 (Aug. 19, 2016), pp. 1-11, //arxiv.org/pdf/1601.06759.pdf [retrieved on Retrieved from the Internet.
Paudel Krishna et al:"Stitching of X-ray Images", uppsala universitet, Thesis Uppsala Universitet, p. 1-78, Nov. 1, 2012.

* cited by examiner

MEDICAL IMAGE ENHANCEMENT

TECHNICAL FIELD

The present invention relates generally to medical image enhancement, and more particularly to artificial intelligence-based systems and methods for generating an augmented medical image having an expanded field of view.

BACKGROUND

Medical images are typically acquired for a specific medical procedure focusing on a specific body part of a patient. Such medical images are acquired having an initial field of view depicting an observed area, such as the specific body part of the patient. The initial field of view represents the region within an outer perimeter of the observed area of the medical image. However, the initial field of view of such medical images is often limited in scope.

Conventional approaches for augmenting images typically focus on image completion (i.e., inpainting), where one or more missing portions within the initial field of view of an image are reconstructed. Such conventional approaches to image completion are limited to generating imaging data for the missing portion within the initial field of view where the missing portion is surrounded on all sides by a priori imaging data.

BRIEF SUMMARY OF THE INVENTION

In accordance with one or more embodiments, systems and methods are provided for generating an augmented medical imaging having an expanded field of view, which comprises an initial field of view of an initial medical image and an augmentation region outside of the initial field of view. Providing such an expanded field of view is beneficial in a number of use cases. For example, an expanded field of view would provide additional context to a clinician on anatomical structures depicted in the initial medical images. In another example, an expanded field of view would improve performance of medical imaging analysis algorithms that are designed for images having a larger field of view, such as, e.g., landmark detectors and image registration algorithms. There are no known conventional methods for providing an expanded field of view depicting an augmentation region that is outside of the initial field of view.

In accordance with one or more embodiments, systems and methods are provided for enhancing a medical image. An initial medical image having an initial field of view is received. An augmented medical image having an expanded field of view is generated using a trained machine learning model. The expanded field comprises the initial field of view and an augmentation region. The augmented medical image is output.

The augmentation region of the augmented medical image may comprise a region immediately surrounding the initial field of view of the initial medical image. The augmented medical image may be a different modality than a modality of the initial medical image. In one embodiment, the augmented medical image is generated based on a prior initial medical image and a prior augmented medical image.

The trained machine learning model may be a trained generative adversarial network. The trained generative adversarial network may be based on at least one of a U-Net, a context encoder, and a variational auto-encoder. In one embodiment, the augmented medical image may be refined using another trained machine learning model.

In one embodiment, the initial field of view may be a high-quality region of an x-ray image and the expanded field of view comprises the high-quality region and the augmentation region. In another embodiment, the initial medical image comprises an anatomical model.

These and other advantages of the invention will be apparent to those of ordinary skill in the art by reference to the following detailed description and the accompanying drawings.

DETAILED DESCRIPTION

The present invention generally relates to systems and methods for medical image enhancement. Embodiments of the present invention are described herein to give a visual understanding of such systems and methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be discussed with respect to the enhancement of medical images, the present invention is not so limited. Embodiments of the present invention may be applied for the enhancement of any type of image.

Figure 1:
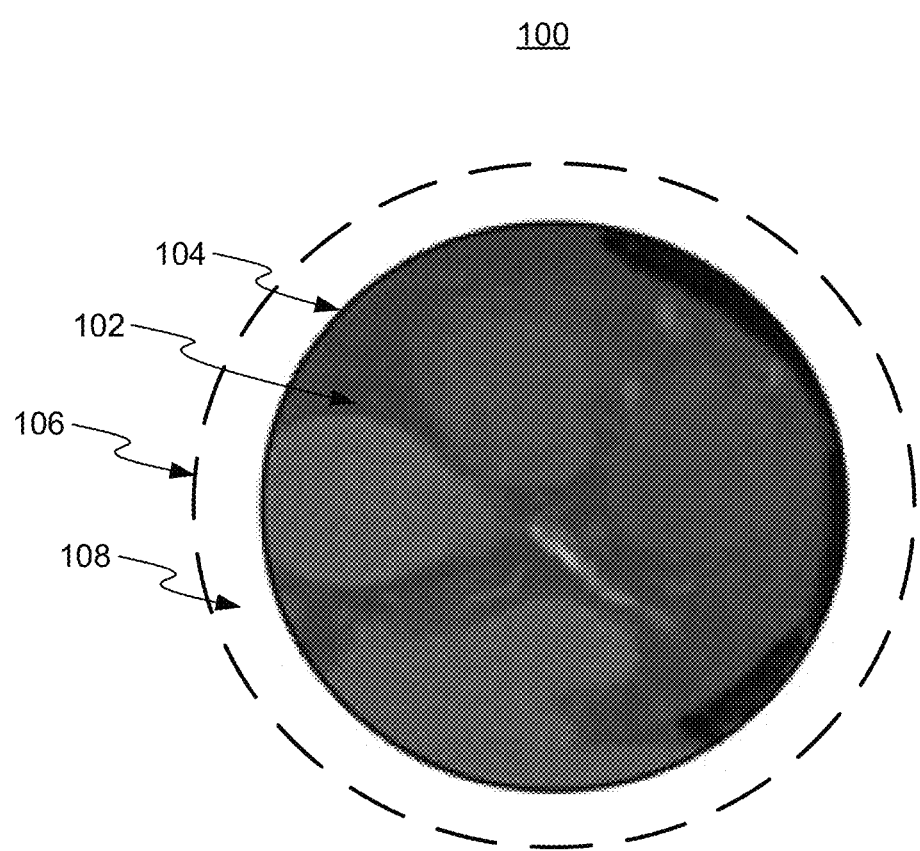
FIG. 1 shows an exemplary medical image of a patient.

FIG. 1 shows an initial DynaCT medical image 100 of a patient (or any other subject). Initial medical image 100 may be acquired to facilitate a clinical examination of the patient, such as, e.g., angiography. Initial medical image 100, as initially acquired, has an initial field of view 102, defined as the region within an outer perimeter 104 of the observed area of initial medical image 100. Initial field of view 102 of initial medical image 100 may be limiting for some medical imaging analysis tasks.

Embodiments of the present invention employ one or more neural networks for generating an augmented medical image having an expanded field of view comprising initial field of view 102 and augmentation region 108. Augmentation region 108 is the region between outer perimeter 104 of initial field of view 102 and outer perimeter 106 of the expanded field of view, and does not include any region within outer perimeter 104 (e.g., any region surrounded by imaging data of initial medical image 100). By generating the augmented medical image, imaging data for augmentation region 108 is thereby generated to augment initial medical image 100. Advantageously, an augmented medical imaging having an expanded field of view comprising initial field of view 102 and augmentation region 108 would, e.g., provide additional context to a clinician on anatomical structures depicted within initial field of view 102 of initial medical image 100 and improve performance of medical imaging analysis algorithms (e.g., landmark detectors and image registration algorithms). The generation of the augmented medical image is a complex task since augmentation region 108 only has imaging data of initial medical image 100 on, e.g., one side, and is not surrounded on all sides by the imaging data. The generation of the augmented medical image becomes more difficult as the distance between the pixels that it has to generate in augmentation region 108 and outer perimeter 104 becomes larger.

Figure 2:
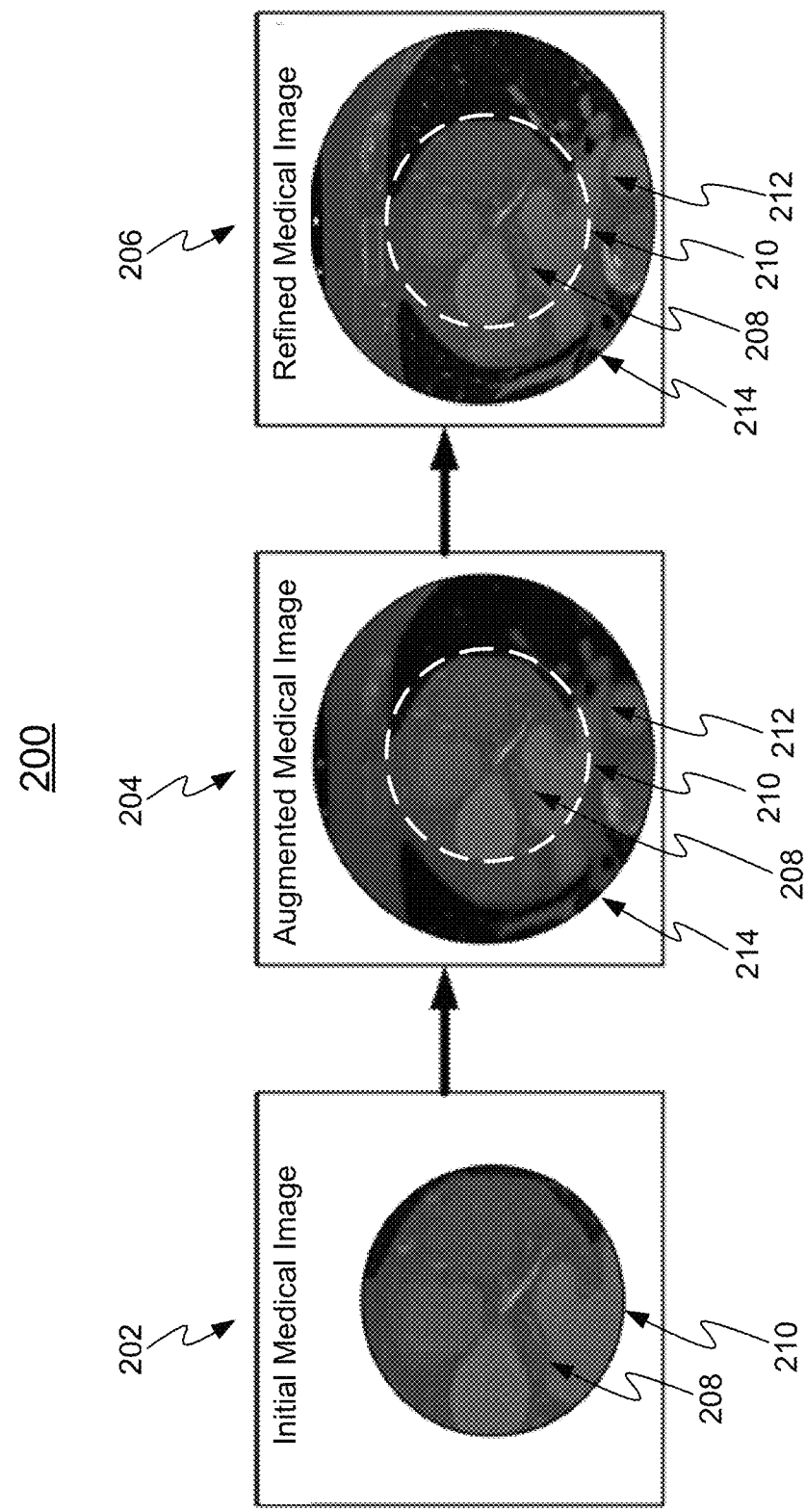
FIG. 2 shows an illustrative high level workflow for enhancing a medical image, in accordance with one or more embodiments.
Figure 3:
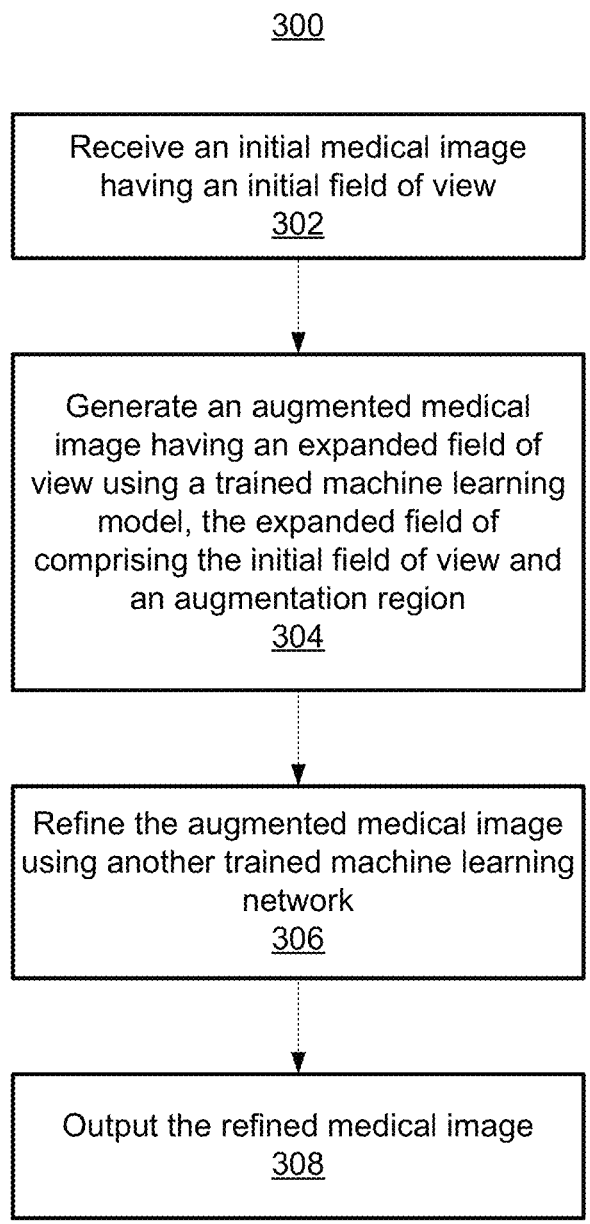
FIG. 3 shows a method for implementing the workflow shown in FIG. 2, in accordance with one or more embodiments.

FIGS. 2 and 3 will now be simultaneously discussed. FIG. 2 shows an illustrative high level workflow 200 for enhancing a medical image, in accordance with one or more embodiments. FIG. 3 shows a method 300 for implementing workflow 200 of FIG. 2. Method 300 may be performed by any suitable computing device, such as, e.g., computer 902 of FIG. 9.

At step 302 of FIG. 3, an initial medical image having an initial field of view is received. An exemplary initial medical image 202 having initial field of view 208 is shown in workflow 200 of FIG. 2. Initial field of view 208 is defined as the region within an outer perimeter 210 of the observed area of initial medical image 202. The initial medical image 202 may be a two dimensional (2D) or three dimensional (3D) image of any suitable modality, such as, e.g., DynaCT, computed tomography (CT), x-ray, magnetic resonance imaging (MRI), ultrasound (US), single-photon emission computed tomography (SPECT), positron emission tomography (PET), or any other suitable modality or combination of modalities. Initial medical image 202 may be received directly from an image acquisition device (e.g., image acquisition device 914 of FIG. 9), or may be received by loading initial medical image 202 from a memory or storage of a computer system, or by receiving initial medical image 202 at a computer system via a network transmission from another computer system.

At step 304 of FIG. 3, an augmented medical image having an expanded field of view is generated from the initial medical image using a trained machine learning model. An exemplary augmented medical image 204 is shown in workflow 200 of FIG. 2 having an expanded field of view comprising initial field of view 208 and augmentation region 212. Augmentation region 212 is the region between outer perimeter 210 of initial field of view 208 and outer perimeter 214 of the expanded field of view, and does not include any region within outer perimeter 210 (e.g., any area surrounded by imaging data of initial medical image 202). Augmentation region 212 may be of any size or shape. In one embodiment, augmentation region 212 is the region immediately surrounding outer perimeter 210, as illustratively shown in workflow 200. By generating augmented medical image 204, imaging data for augmentation region 212 is thereby generated to augment initial medical image 202. In some embodiments, an entirely new augmented medical image 204 may be generated by generating augmentation region 212 and regenerating initial field of view 208, while in other embodiments augmented medical image 204 is generated by only generating augmentation region 212 while copying the imaging data of initial field of view 208 from initial medical image 202.

In one embodiment, augmented medical image 204 is generated using the trained machine learning model such that augmented medical image 204 is a different modality than the modality of the initial medical image 202. Accordingly, the trained machine learning model generates augmented medical image 204 to simultaneously augment the initial medical image 202 in augmentation region 212 while also performing style transfer of initial medical image 202 from one modality to another (e.g., DynaCT to CT).

The trained machine learning model may be any suitable machine learning model, such as, e.g., a neural network. In one embodiment, the trained machine learning model is a generative adversarial network (GAN), as described in more detail below with respect to FIG. 5. The GAN may be implemented using a U-Net, a context encoder, and/or a variational auto-encoder (VAE).

The trained machine learning model is trained in a prior training stage using pairs of training images. The training images may be generated by cropping initial training images such that each initial training image and its corresponding cropped training image form a pair of training images. The initial training image may be cropped according to various shapes and sizes. The initial training images may be patient-specific training images or synthetically generated training images.

At step 306 of FIG. 3, optionally, augmented medical image 204 is refined using another trained machine learning model to generate refined medical image 206. Refined medical image 206 may be generated by de-noising the augmented medical image 204, applying super-resolution imaging techniques on augmented medical image 204, or any other form of refinement or enhancement as is known in the art.

The other trained machine learning model may be any suitable machine learning model, such as, e.g., a neural network. The other trained machine learning model is trained in a prior training stage using pairs of training images. The training images may be generated by blurring initial training images such that each initial training image and its corresponding blurred training image form a pair of training images. The training images may be patient-specific training images or synthetic training images. In one embodiment, a same set of initial training images is used for training the other machine learning model and for training the machine learning network (applied at step 304).

At step 308 of FIG. 3, the refined medical image 206 is output. The refined medical image 206 can be output by displaying the refined medical image 206 on a display device of a computer system, storing the refined medical image 206 on a memory or storage of a computer system, or by transmitting the refined medical image 206 to a remote computer system, e.g., for further processing.

In accordance with one embodiment, method 300 may be applied to generate hyper-realistic collimated images. X-ray imaging is very sensitive to collimation. When x-ray beams targeting a patient are not perfectly aligned, the generated image has two regions: a high-quality region resulting from a higher density of x-ray beams, and a low-quality region resulting from a lower density of x-ray beams. Method 300 may be applied to solve the collimation issue by considering the high-quality region of the x-ray image to be the initial field of view 208 of the initial medical image 202 (received at step 302). Method 300 continues at step 304 to generate an augmented medical image 204 having expanded field of view comprising the high-quality region of the x-ray region and augmentation region 212, conditioned on the low-quality region of the x-ray image. For example, the low-quality region of the x-ray image may be used as an additional input into the machine learning models, or may be used in a post-process step to further refine the output of the machine learning models. Accordingly, method 300 may act as a collimation calibration step, resulting in a high-quality hyper-realistic collimated image.

In accordance with one embodiment, method 300 may be applied to enhance information and knowledge extracted from medical images, such as, e.g., an anatomical model. Given a medical image depicting, e.g., a portion of an arterial tree, an anatomical model (in one, two, or three dimensions) of the arterial tree may be reconstructed from the medical image. Method 300 may be applied to enhance the anatomical model by considering the anatomical model to be the initial field of view 208. Accordingly, at step 304, an augmented anatomical model is generated having an expanded field of view comprising initial field of view 208 and augmentation region 212. In this embodiment, the refining step 306 may not be performed. The generated data may have a different dimensionality than the anatomical model. For example, the anatomical model may be 3D while the generated data may have zero dimensionality (e.g., resistances, compliances, etc.). The machine learning network applied at step 304 may be trained during a prior training stage starting with a large existing dataset of initial training images. To generate the training data, a cropped version of each initial training image is generated. A reconstructed anatomical model is generated from the cropped training images (with the desired dimensionality). A reconstruction anatomical model is generated for the augmentation region of the cropped training images (with the same or different dimensionality) using the initial training images. Thus, method 300 may be applied to generate an enhanced medical image and an enhanced anatomical model.

In accordance with one embodiment, where motion of anatomical structures is of interest, medical imaging techniques, such as, e.g., echocardiography and angiography, are applied to acquired multiple initial medical images of an object of interest over a period of time. Workflow 200 of FIG. 2 and method 300 of FIG. 3 may be modified to generate an augmented medical image and refined medical image based on one or more prior initial medical images and prior augmented medical images, which correspond to previous points in time, as shown in FIG. 4.

Figure 4:
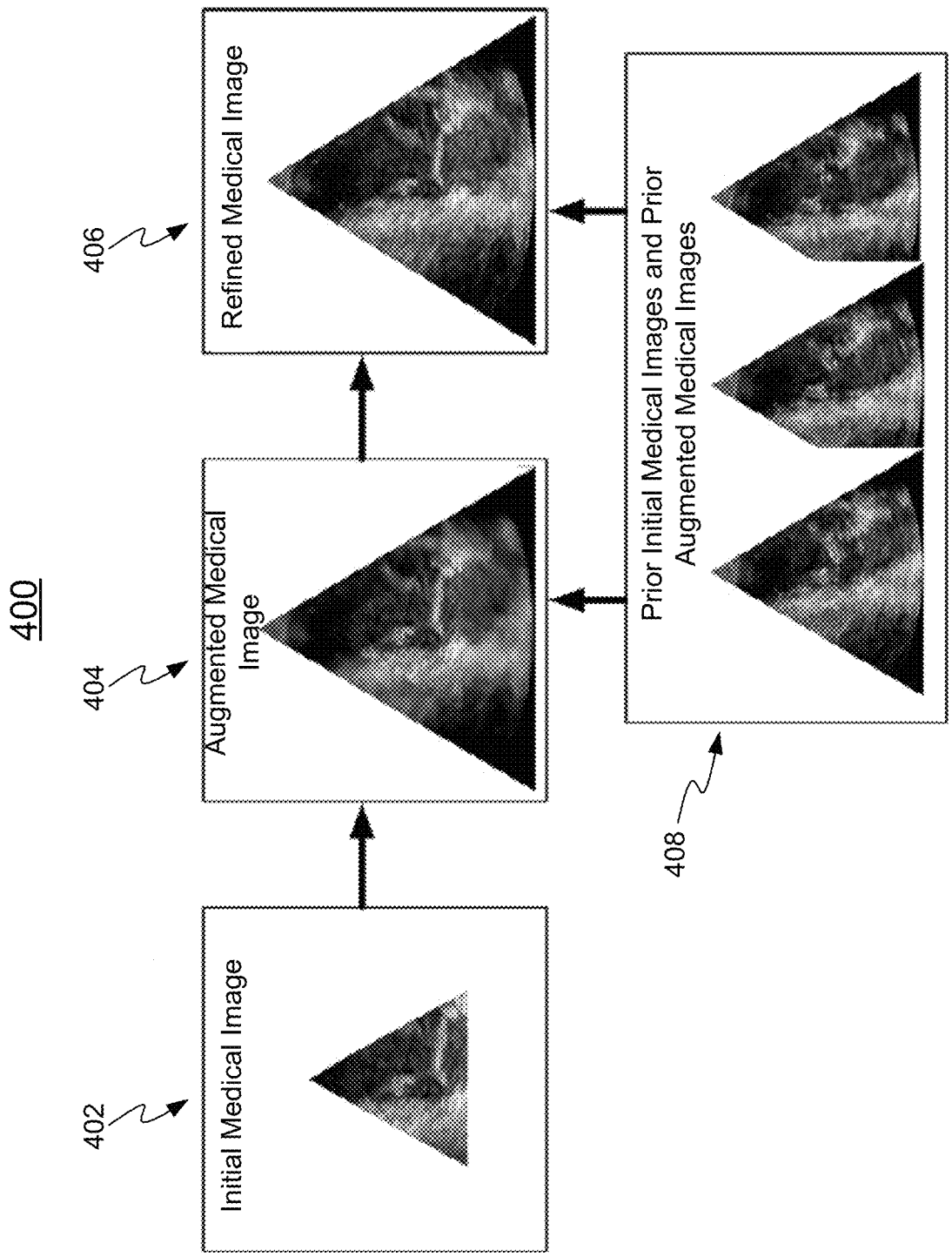
FIG. 4 shows a high level workflow for enhancing a medical image using information from previous time points, in accordance with one or more embodiments.

FIG. 4 shows a high level workflow 400 for enhancing a medical image using one or more prior initial medical images and prior augmented medical images, in accordance with one or more embodiments. In workflow 400, an initial medical image 402 having an initial field of view is received. An augmented medical image 404 having an expanded field of view is generated from an initial medical image 402 using a trained machine learning model (e.g., neural network), and based on prior initial medical images and prior augmented medical images 408, which correspond to one or more previous points in time. Augmented image 404 is then refined using another machine learning model (e.g., neural network) based on prior initial medical images and prior augmented medical images 408 to generate refined medical image 406.

In one embodiment, the one or more trained machine learning networks used to generate augmented medical image 404 and/or refined medical view image 406 in workflow 400 may each comprise a neural network (e.g., a GAN) implemented with a long short-term memory (LSTM) network, which provides long term memory controlled by opening or closing an input gate, an output gate, and/or a forget gate. Advantageously, the LSTM network enables prior initial medical images and prior augmented medical images 408 to be stored and subsequently used to generate more accurate images (i.e., augmented medical image 404 and refined medical image 406). It should be understood that the present invention is not limited to LSTM networks; any type of recurrent neural network (RNN) architecture may be employed, such as, e.g., a gated recurrent unit (GRU).

Figure 5:
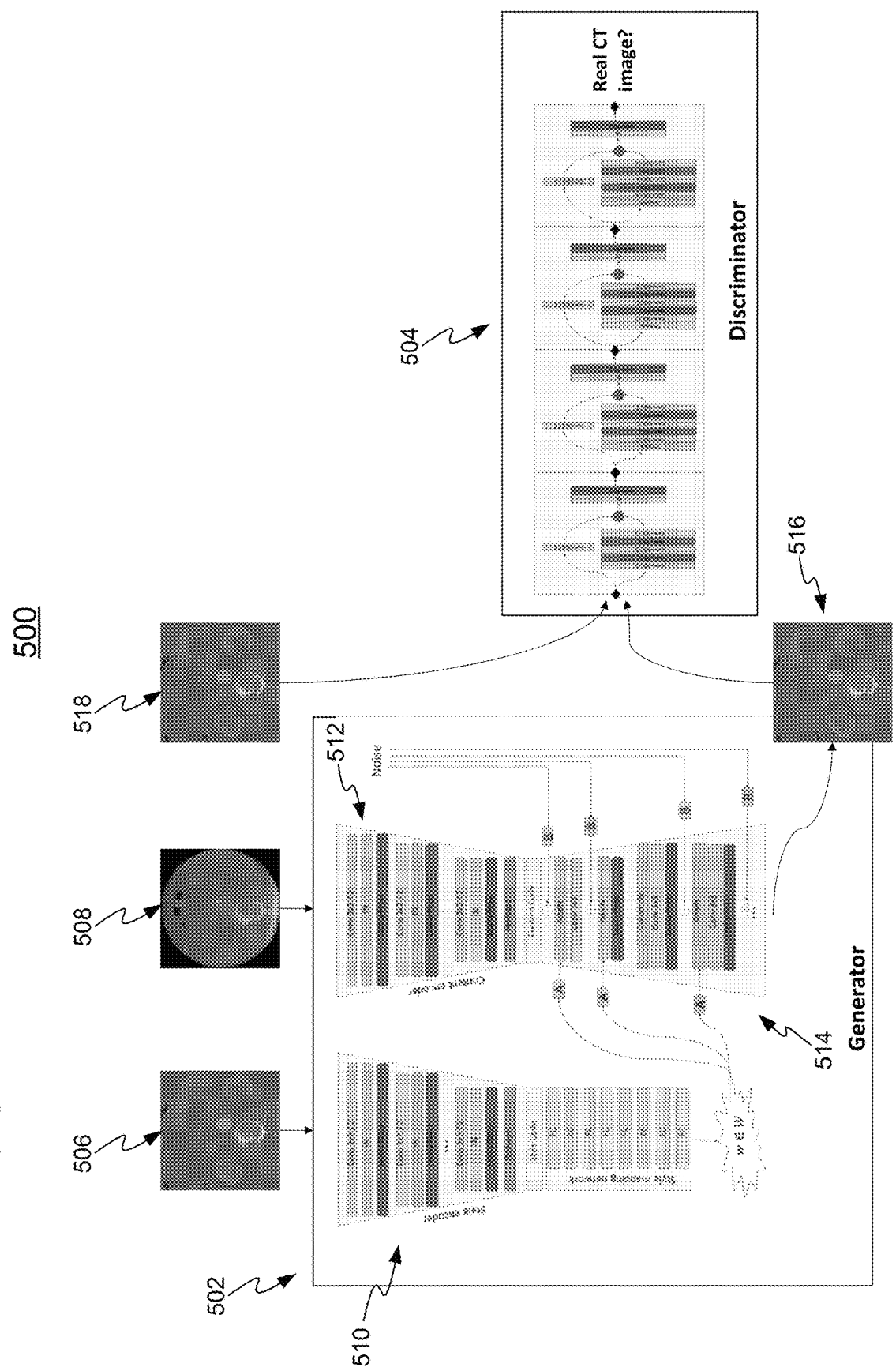
FIG. 5 shows a functional block diagram for training a generative adversarial network (GAN) for generating an augmented medical image, in accordance with one or more embodiments.

FIG. 5 shows a GAN 500 for generating an augmented medical image, in accordance with one or more embodiments. In one embodiment, GAN 500 is the trained machine learning model applied at steps 304 and/or 306 of FIG. 3. GANs represent a framework for creating generative models via an adversarial process. GAN 500 comprises two modules in the form of deep networks: a generator 502 for generation of a synthesized image 516 in a target modality and a discriminator 504 for distinguishing between a real image 518 and the synthesized image 516. Generator 502 generates synthesized image 516 in the target modality (e.g., CT) from an input image 508 in an initial modality (e.g., DynaCT). Discriminator 504 inputs the synthesized image 516 generated by generator 502 and a real image 518 and classifies one image as real and the other image as fake (synthesized). Generator 502 and discriminator 504 are simultaneously trained such that while discriminator 504 is improving in terms of fake image detection, generator 502 is improving in terms of producing realistic looking images capable of fooling discriminator 504. Accordingly, generator 502 and discriminator 504 are trained with adversarial loss to force generator 502 to learn the most meaningful features. Discriminator 504 is only used during the training stage, and is not used during the online or inference stage, e.g., to generate augmented medical images.

As shown in FIG. 5, generator 502 comprises a style encoder 510 and content encoder 512. Style encoder 510 receives a reference image 506 in the target domain and encodes reference image 506 to a style code representing low level features of reference image 506. Content encoder 512 receives real image 508 in the initial domain and encodes real image 508 to a content code representing low level features of real image 508. Decoder 514 generates synthesized image 516 based on the content code from content encoder 512 and weights based on style code from style encoder 510. It should be understood that generator 502 may be implemented using any suitable network.

In one embodiment, generator 502 is implemented as a U-Net. A U-Net is a convolutional neural network comprising a contracting path and an expansive path. The contracting path reduces spatial information of the input image while increasing feature information. The expansive path combines the spatial and feature information through a sequence of up-convolutions and concatenations with high-resolution features from the contracting path. Due to its skip connections, the U-Net is suitable for image completion tasks.

In another embodiment, generator 502 is implemented as a context encoder. A context encoder is a convolutional neural network trained to generate the contents of an arbitrary image region conditioned on its surroundings. Given an image, the network down-samples it to a specific dimension using an encoder, followed by a number of channel-wise fully-connected layers. Finally, a decoder produces the missing region of the image. Due to the fully connected layers, the mapping that generates the missing region of the image is highly conditioned on its surroundings.

In another embodiment, generator 502 is implemented as a VAE. The VAE comprises an encoder and a decoder. The encoder encodes an input image as a set of parameters of a statistical distribution (e.g., a mean and a variance). The decoder randomly samples a point from the statistical distribution to reconstruct the input image.

Figure 6:
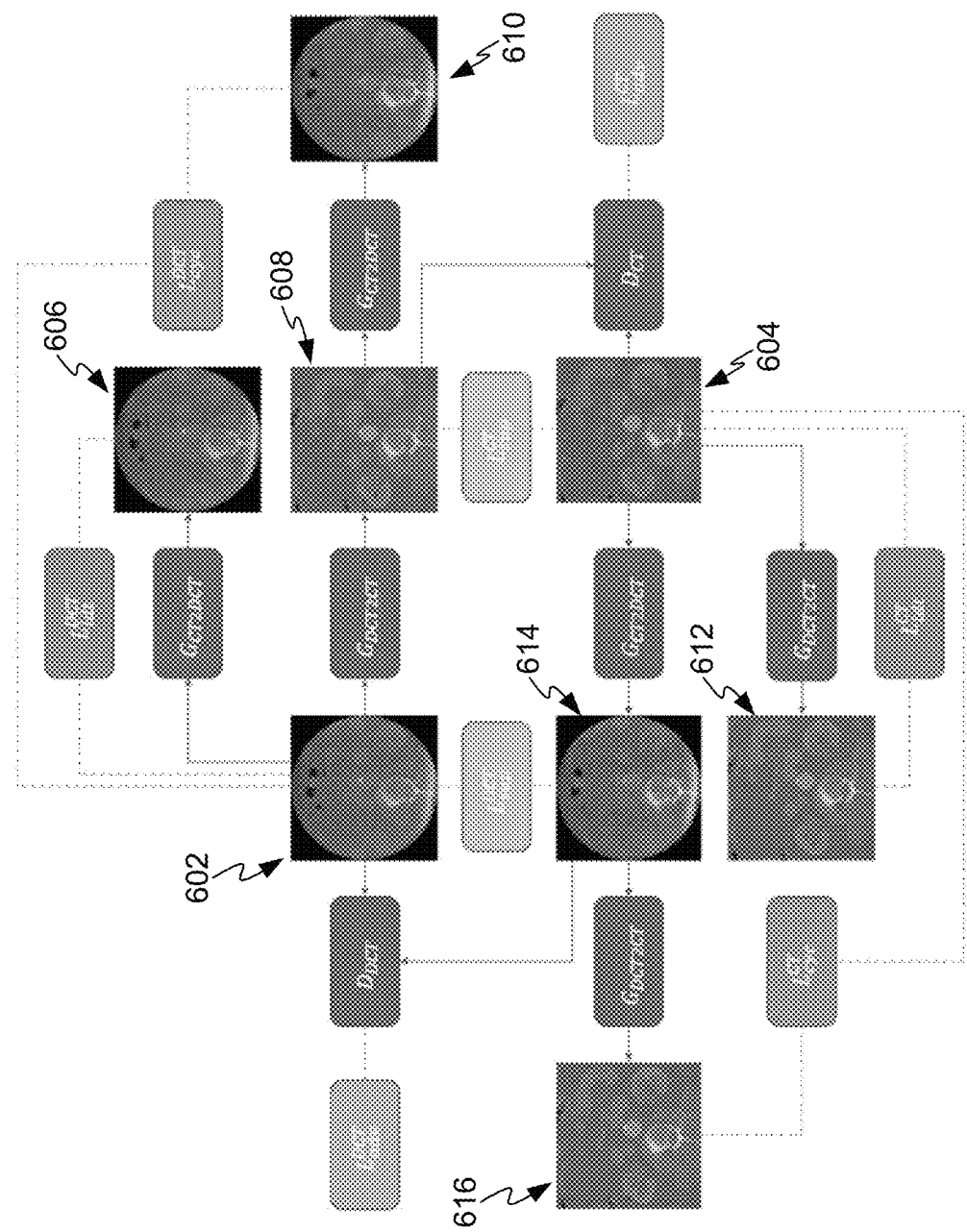
FIG. 6 shows a functional block diagram for training a CycleGAN for generating an augmented medical image, in accordance with one or more embodiments.

In one embodiment, the GAN shown in block diagram 500 may be a CycleGAN to enforce cycle consistency, such that an input image in a first modality translated to a second modality and then translated back to the first modality should return the original input image. FIG. 6 shows a functional block diagram 600 for training a CycleGAN for generating an augmented medical image, in accordance with one or more embodiments.

Functional block diagram 600 comprises generator $G_{DCT2CT}$ for generating synthesized augmented CT images (or images of any other target modality) from an input DynaCT (DCT) image (or an input image of any other initial modality) and generator $G_{CT2DCT}$ for generating synthesized augmented DCT images (or images of any other target modality) from an input CT image (or an input image of any other initial modality). Generators $G_{DCT2CT}$ and $G_{CT2DCT}$ are trained using DCT input image 602 and CT input image 604. Images 602 and 604 are real images.

Generators $G_{DCT2CT}$ and $G_{CT2DCT}$ are trained with discriminators $D_{CT}$ and $D_{DCT}$ for adversarial loss. Discriminator $D_{CT}$ aims to distinguish between synthesized CT images generated by generator $G_{DCT2CT}$ and a real CT image (e.g., synthesized CT image 608 and real input CT image 604), and classifies one image as real and the other as fake. Discriminator $D_{DCT}$ aims to distinguish between synthesized DCT images generated by generator $G_{CT2DCT}$ and a real DCT image (e.g., synthesized DCT image 614 and real input DCT image 602), and classifies one image as real and the other as fake. Discriminators $D_{CT}$ and $D_{DCT}$ will guide generators $G_{DCT2CT}$ and $G_{CT2DCT}$ to generate synthesized images that are indistinguishable from the real images in their corresponding modality. Generators $G_{DCT2CT}$ and $G_{CT2DCT}$ and their discriminators $D_{CT}$ and $D_{DCT}$ are expressed as the objectives of Equations (1) and (2), respectively.

$$\mathcal{L}_{adv}^{CT} = \mathcal{L}_{WGAN}(D_{CT}, G_{DCT2CT}) = -\mathbb{E}_{CT}(D(CT)) + \mathbb{E}_{DCT}(D(G(DCT))) + \lambda \mathbb{E}_{CTlikeDCT}[(\|\nabla_{CTlikeDCT}(D(CTlikeDCT))\| - 1)^2] \quad \text{Equation (1):}$$

$$\mathcal{L}_{adv}^{CT} = \mathcal{L}_{WGAN}(D_{DCT}, G_{CT2DCT}) = -\mathbb{E}_{DCT}(D(DCT)) + \mathbb{E}_{CT}(D(G(DCT))) + \lambda \mathbb{E}_{DCTlikeCT}[(\|\nabla_{DCTlikeCT}(D(DCTlikeCT))\| - 1)^2] \quad \text{Equation (2):}$$

Cycle consistency is introduced such that a synthesized image in the target domain could return back to the exact image in the source domain that it was generated from. Cycle consistency loss $\mathcal{L}_{cyc}^{CT}$ compares a real CT image with a synthesized CT image (generated by translating a real CT image to a synthesized DCT image, and translating the synthesized DCT image to the synthesized CT image) (e.g., real CT image 604 and synthesized CT image 616). Similarly, cycle consistent loss $\mathcal{L}_{cyc}^{DCT}$ compares a real DCT image with a synthesized DCT image (generated by translating a real DCT image to a synthesized CT image, and translating the synthesized CT image to the synthesized DCT image) (e.g., real DCT image 602 and synthesized DCT image 610). Cycle consistency loss for generators $G_{DCT2CT}$ and $G_{CT2DCT}$ are defined by the following loss function.

$$\mathcal{L}_{cyc}(G_{CT2DCT}, G_{DCT2CT}) = \mathbb{E}_{CT}[\|G_{DCT2CT}(G_{CT2DCT}(CT)) - CT\|_1] + \mathbb{E}_{DCT}[\|G_{CT2DCT}(G_{DCT2CT}(DCT)) - DCT\|_1] \quad \text{Equation (3):}$$

Since the CT-like DCT image should be an enhanced version of the DCT image, identity loss is employed to regularize the training procedure. In other words, if a generator sees a real image in the target domain, it should make no changes to it. Identity loss for generators $G_{DCT2CT}$ and $G_{CT2DCT}$ are defined by the following loss function.

$$\mathcal{L}_{idt}(G_{CT2DCT}, G_{DCT2CT}) = \mathbb{E}_{CT}[\|G_{DCT2CT}(CT) - CT\|_1] + \mathbb{E}_{DCT}[\|G_{CT2DCT}(DCT) - DCT\|_1] \quad \text{Equation (4):}$$

Generators $G_{DCT2CT}$ and $G_{CT2DCT}$ are also trained with supervision according to the following supervision loss.

$$\mathcal{L}_{sup}(G_{CT2DCT}, G_{DCT2CT}) = \mathbb{E}_{CT}[\|G_{CT2DCT}(CT) - DCT\|_1] + \mathbb{E}_{DCT}[\|G_{DCT2CT}(DCT) - CT\|_1] \quad \text{Equation (5):}$$

A composite objective function is defined below in Equation (6), as a composite of Equations (1)-(5), to train generators $G_{DCT2CT}$ and $G_{CT2DCT}$, where parameter $\lambda$ represents weights for each loss.

$$\mathcal{L}_{total} = \lambda_{adv} \mathcal{L}_{adv}^{CT} + \lambda_{adv} \mathcal{L}_{adv}^{DCT} + \lambda_{sup} \mathcal{L}_{sup}^{CT} + \lambda_{sup} \mathcal{L}_{sup}^{DCT} + \lambda_{cyc} \mathcal{L}_{cyc}^{CT} + \lambda_{cyc} \mathcal{L}_{cyc}^{DCT} + \lambda_{idt} \mathcal{L}_{idt}^{CT} + \lambda_{idt} \mathcal{L}_{idt}^{DCT} \quad \text{Equation (6):}$$

Embodiments of the present invention were experimentally validated using two different configurations of GANs.

Figure 7:
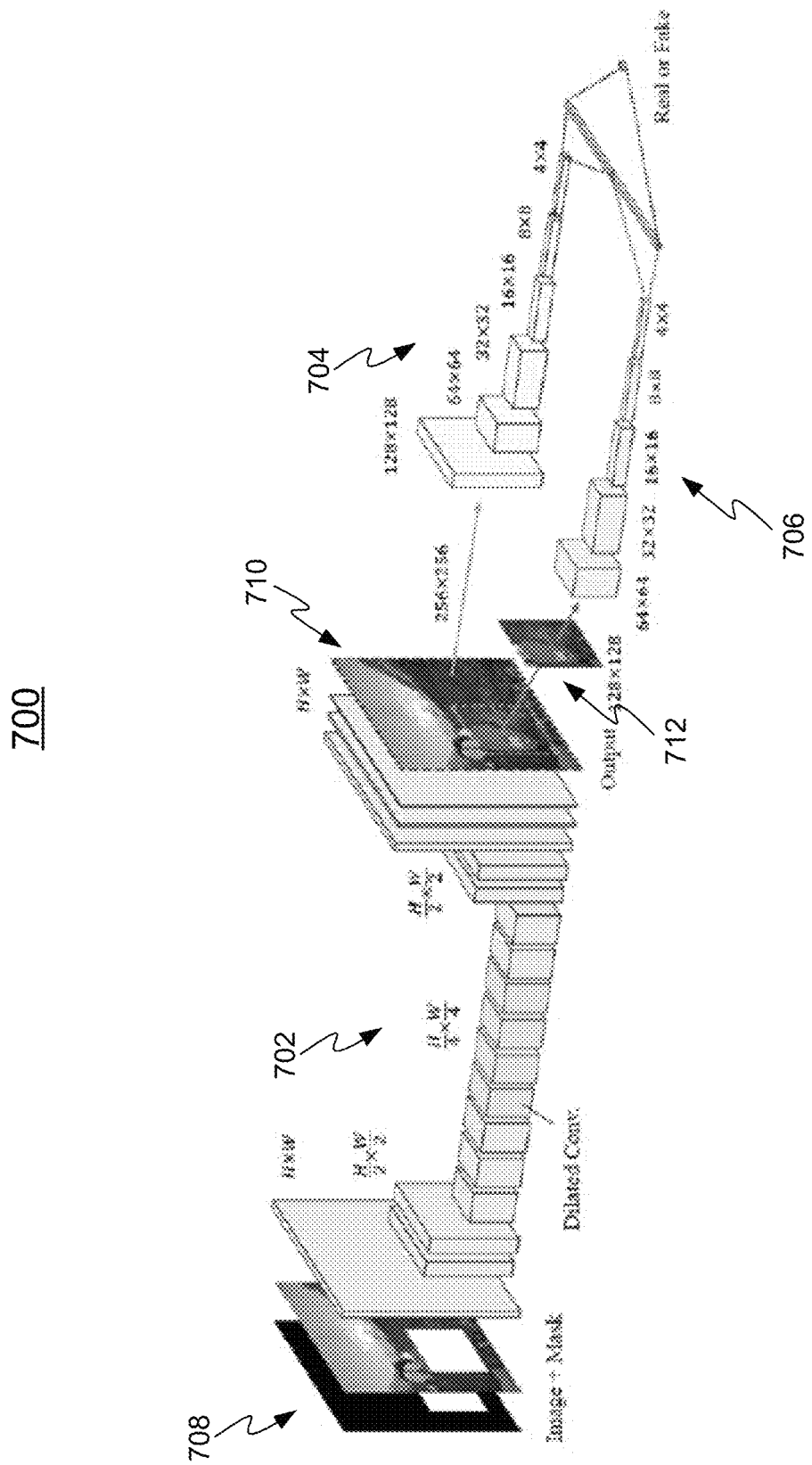
FIG. 7 shows a network architecture for training a Pix2Pix-GAN, in accordance with one or more embodiments.
Figure 8:
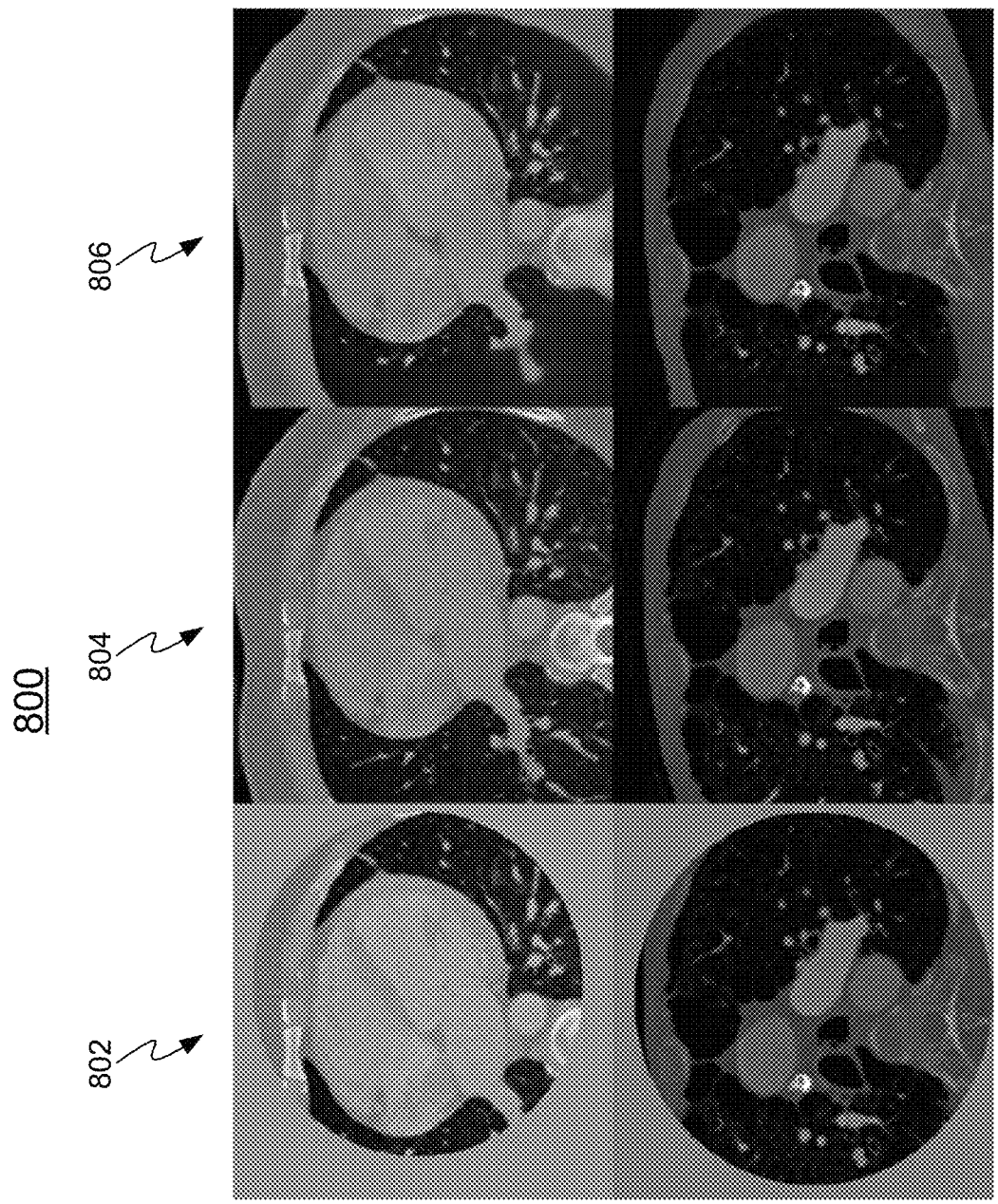
FIG. 8 shows a comparison of images resulting from applying a Pix2Pix-GAN implemented with a context encoder applied in accordance with embodiments of the invention with ground truth images.

In a first experiment, a Pix2Pix-GAN implemented with a context encoder was applied for generating an augmented medical image. FIG. 7 shows a network architecture for training a Pix2Pix-GAN 700, in accordance with one or more embodiments. Pix2Pix-GAN 700 comprises generator 702 and discriminators 704 and 706. Generator 702 is a fully convolutional context encoder and discriminators 704 and 708 are convolutional networks that output a probability indicating whether the image (generated by generator 702) is real or fake (synthesized). Generator 702 receives as input a training image 708 having a missing region and outputs a synthetic image 712 having augmented region 714. To improve the quality of results, two discriminators 704 and 706 are employed for recognizing fake images. Discriminator 704 is a global discriminator that takes as input the entire synthetic image 712 to ensure that at a global level the image 712 looks realistic, while discriminator 706 takes as input only augmented region 714 to improve the local coherence. FIG. 8 shows a comparison 800 of images resulting from applying embodiments of the present invention using a Pix2Pix-GAN implemented with a context encoder (i.e., Pix2Pix-GAN 700) with ground truth images. Column 802 shows input images, column 804 shows ground-truth images, and column 806 shows generated images using Pix2Pix-GAN 700.

Figure 9:
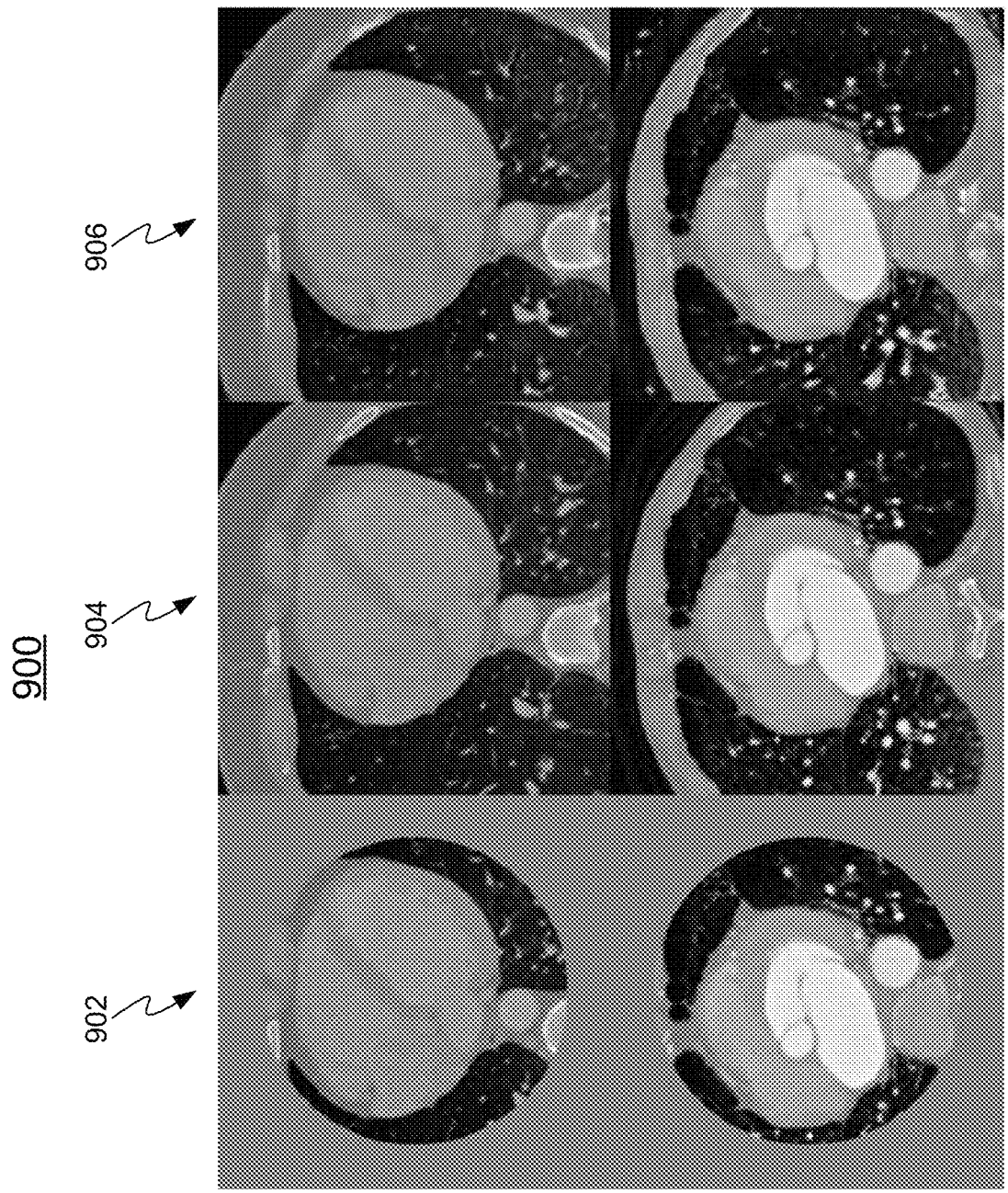
FIG. 9 shows a comparison of images resulting from applying a Pix2Pix-GAN implemented with a U-Net architecture applied in accordance with embodiments of the invention with ground truth images.

In a second experiment, a Pix2Pix-GAN implemented with a U-Net was applied for generating an augmented medical image. In particular, in this configuration, the generator of the Pix2Pix-GAN was implemented using a U-Net architecture. The discriminator splits the input image into patches which are classified separately. In other words, the discriminator penalizes the structure only at the patch level, trying to determine whether each of the N×N patches in an image is real or fake (synthesized). The last layer of the network averages all responses to provide the output. FIG. 9 shows a comparison 900 images resulting from applying embodiments of the present invention using the Pix2Pix-GAN implemented with a U-Net with ground truth images. Column 902 shows input images, column 904 shows ground-truth images, and column 906 shows generated images using the Pix2Pix-GAN implemented with a U-Net.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2-4. Certain steps or functions of the methods and workflows described herein, including one or more of the steps or functions of FIGS. 2-4, may be performed by a server or by another processor in a network-based cloud-computing system. Certain steps or functions of the methods and workflows described herein, including one or more of the steps of FIGS. 2-4, may be performed by a client computer in a network-based cloud computing system. The steps or functions of the methods and workflows described herein, including one or more of the steps of FIGS. 2-4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2-4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 10:
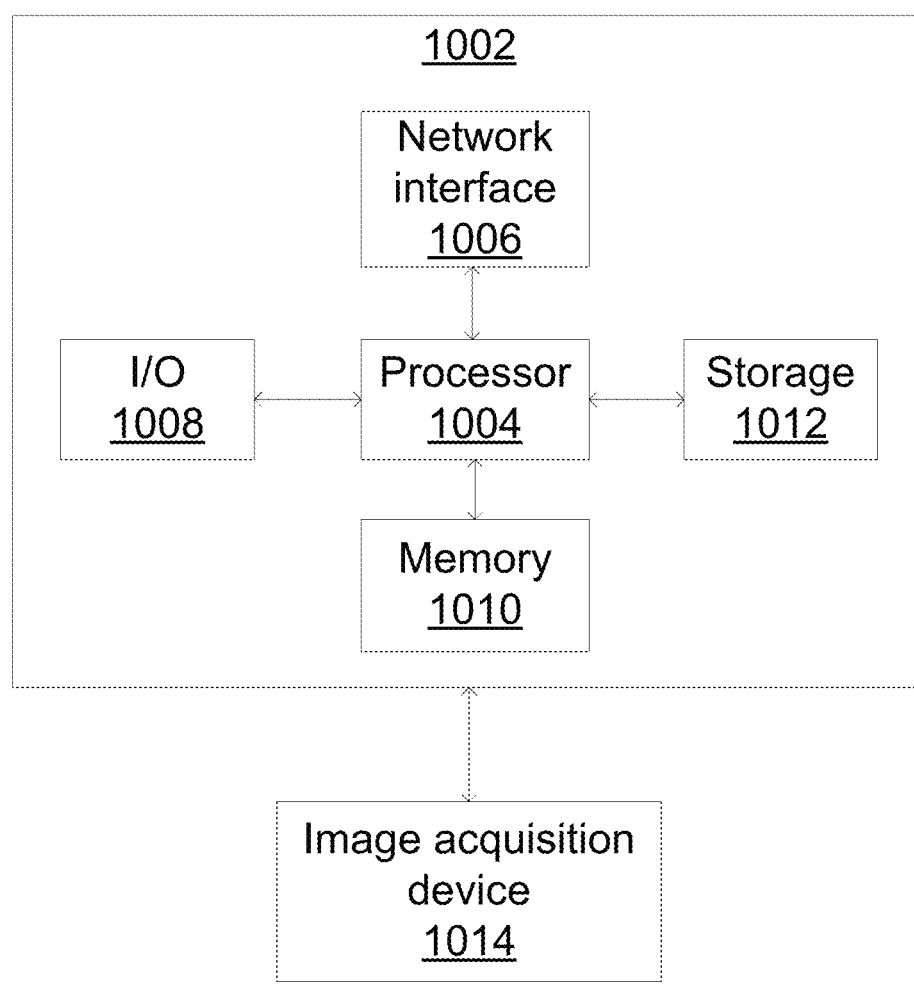
FIG. 10 shows a high-level block diagram of a computer.

A high-level block diagram of an example computer 902 that may be used to implement systems, apparatus, and methods described herein is depicted in FIG. 10. Computer 1002 includes a processor 1004 operatively coupled to a data storage device 1012 and a memory 1010. Processor 1004 controls the overall operation of computer 1002 by executing computer program instructions that define such operations. The computer program instructions may be stored in data storage device 1012, or other computer readable medium, and loaded into memory 1010 when execution of the computer program instructions is desired. Thus, the method and workflow steps or functions of FIGS. 2-4 can be defined by the computer program instructions stored in memory 1010 and/or data storage device 1012 and controlled by processor 1004 executing the computer program instructions. For example, the computer program instructions can be implemented as computer executable code programmed by one skilled in the art to perform the method and workflow steps or functions of FIGS. 2-4. Accordingly, by executing the computer program instructions, the processor 1004 executes the method and workflow steps or functions of FIGS. 2-4. Computer 1004 may also include one or more network interfaces 1006 for communicating with other devices via a network. Computer 1002 may also include one or more input/output devices 1008 that enable user interaction with computer 1002 (e.g., display, keyboard, mouse, speakers, buttons, etc.).

Processor 1004 may include both general and special purpose microprocessors, and may be the sole processor or one of multiple processors of computer 1002. Processor 1004 may include one or more central processing units (CPUs), for example. Processor 1004, data storage device 1012, and/or memory 1010 may include, be supplemented by, or incorporated in, one or more application-specific integrated circuits (ASICs) and/or one or more field programmable gate arrays (FPGAs).

Data storage device 1012 and memory 1010 each include a tangible non-transitory computer readable storage medium. Data storage device 1012, and memory 1010, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1008 may include peripherals, such as a printer, scanner, display screen, etc. For example, input/output devices 1008 may include a display device such as a cathode ray tube (CRT) or liquid crystal display (LCD)

monitor for displaying information to the user, a keyboard, and a pointing device such as a mouse or a trackball by which the user can provide input to computer 1002.

An image acquisition device 1014 can be connected to the computer 1002 to input image data (e.g., medical images) to the computer 1002. It is possible to implement the image acquisition device 1014 and the computer 1002 as one device. It is also possible that the image acquisition device 1014 and the computer 1002 communicate wirelessly through a network. In a possible embodiment, the computer 1002 can be located remotely with respect to the image acquisition device 1014.

Any or all of the systems and apparatus discussed herein may be implemented using one or more computers such as computer 1002.

One skilled in the art will recognize that an implementation of an actual computer or computer system may have other structures and may contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for enhancing a medical image, comprising:
receiving an initial medical image having an initial field of view;
generating an augmented medical image having an expanded field of view using a trained machine learning model, the expanded field of view comprising the initial field of view and an augmentation region, the trained machine learning model generating imaging data between an outer perimeter of the initial field of view and an outer perimeter of the expanded field of view and immediately surrounding the initial field of view in the augmentation region; and
outputting the augmented medical image.

2. The method of claim 1, wherein generating an augmented medical image having an expanded field of view using a trained machine learning model comprises:
generating the augmented medical image such that the augmented medical image is a different modality than a modality of the initial medical image.

3. The method of claim 1, further comprising:
refining the augmented medical image using another trained machine learning model.

4. The method of claim 1, wherein generating an augmented medical image having an expanded field of view using a trained machine learning model comprises:
generating the augmented medical image based on a prior initial medical image and a prior augmented medical image.

5. The method of claim 1, wherein the initial field of view comprises a high-quality region of an x-ray image and the expanded field of view comprises the initial field of view and the augmentation region.

6. The method of claim 1, wherein the initial medical image comprises an anatomical model.

7. The method of claim 1, wherein the trained machine learning model is a trained generative adversarial network.

8. The method of claim 7, wherein the trained generative adversarial network is based on at least one of a U-Net, a context encoder, and a variational auto-encoder.

9. An apparatus for enhancing a medical image, comprising:
means for receiving an initial medical image having an initial field of view;
means for generating an augmented medical image having an expanded field of view using a trained machine learning model, the expanded field of view comprising the initial field of view and an augmentation region, the trained machine learning model generating imaging data between an outer perimeter of the initial field of view and an outer perimeter of the expanded field of view and immediately surrounding the initial field of view in the augmentation region; and
means for outputting the augmented medical image.

10. The apparatus of claim 9, wherein the means for generating an augmented medical image having an expanded field of view using a trained machine learning model comprises:
means for generating the augmented medical image such that the augmented medical image is a different modality than a modality of the initial medical image.

11. The apparatus of claim 9, further comprising:
means for refining the augmented medical image using another trained machine learning model.

12. The apparatus of claim 9, wherein the means for generating an augmented medical image having an expanded field of view using a trained machine learning model comprises:
means for generating the augmented medical image based on a prior initial medical image and a prior augmented medical image.

13. A non-transitory computer readable medium storing computer program instructions for enhancing a medical image, the computer program instructions when executed by a processor cause the processor to perform operations comprising:
receiving an initial medical image having an initial field of view;
generating an augmented medical image having an expanded field of view using a trained machine learning model, the expanded field of view comprising the initial field of view and an augmentation region, the trained machine learning model generating imaging data between an outer perimeter of the initial field of view and an outer perimeter of the expanded field of view and immediately surrounding the initial field of view in the augmentation region; and
outputting the augmented medical image.

14. The non-transitory computer readable medium of claim 13, wherein generating an augmented medical image having an expanded field of view using a trained machine learning model comprises:
generating the augmented medical image such that the augmented medical image is a different modality than a modality of the initial medical image.

15. The non-transitory computer readable medium of claim 13, wherein the initial field of view comprises a high-quality region of an x-ray image and the expanded field of view comprises the initial field of view and the augmentation region.

16. The non-transitory computer readable medium of claim 13, wherein the initial medical image comprises an anatomical model.

17. The non-transitory computer readable medium of claim 13, wherein the trained machine learning model is a trained generative adversarial network.

18. The non-transitory computer readable medium of claim 17, wherein the trained generative adversarial network is based on at least one of a U-Net, a context encoder, and a variational auto-encoder.

* * * * *